(12) United States Patent
Ashraf et al.

(10) Patent No.: US 9,968,404 B2
(45) Date of Patent: May 15, 2018

(54) OPTICAL FIBER WITH SMOOTH TIP

(71) Applicant: LUMENIS LTD., Yokneam Ilit (IL)

(72) Inventors: Naim Ashraf, Bonn (DE); Georg Kuka, Berlin (DE); Arkady Khachaturov, Haifa (IL)

(73) Assignee: LUMENIS LTD. (IL)

(*) Notice: Subject to any disclaimer, the term of this patent is extended or adjusted under 35 U.S.C. 154(b) by 482 days.

(21) Appl. No.: 14/541,038

(22) Filed: Nov. 13, 2014

(65) Prior Publication Data

US 2015/0141974 A1 May 21, 2015

Related U.S. Application Data

(60) Provisional application No. 61/904,569, filed on Nov. 15, 2013.

(51) Int. Cl.
*A61B 18/24* (2006.01)
*H01S 3/067* (2006.01)
*A61B 18/22* (2006.01)

(52) U.S. Cl.
CPC .............. *A61B 18/24* (2013.01); *A61B 18/22* (2013.01); *H01S 3/06708* (2013.01); *A61B 2018/2205* (2013.01); *A61B 2018/2255* (2013.01)

(58) Field of Classification Search
CPC . A61B 18/24; A61B 18/22; A61B 2018/2255; A61B 2018/2205; H01S 3/06708
See application file for complete search history.

(56) References Cited

U.S. PATENT DOCUMENTS

| 4,735,201 A | 4/1988 | O'Reilly | |
|---|---|---|---|
| 5,320,620 A | 6/1994 | Long et al. | |
| 2002/0072791 A1* | 6/2002 | Eder | A61B 17/12022 623/1.15 |
| 2009/0270901 A1* | 10/2009 | Kelleher | A61B 17/12022 606/191 |
| 2010/0100194 A1* | 4/2010 | Kleinman | A61F 2/82 623/23.7 |
| 2011/0242532 A1* | 10/2011 | McKenna | A61B 5/0075 356/319 |

FOREIGN PATENT DOCUMENTS

| DE | 10129029 | 12/2002 |
|---|---|---|
| WO | 2011161126 | 12/2011 |

* cited by examiner

*Primary Examiner* — Scott T Luan
(74) *Attorney, Agent, or Firm* — ISUS Intellectual Property PLLC

(57) ABSTRACT

A laser fiber has a distal end having a laser fiber face. A tip addition is attached to or formed onto the fiber face. The material of the tip addition one of fragments or melts when laser energy from a suitable laser device is passed through the laser fiber and through the tip addition.

16 Claims, 2 Drawing Sheets

OPTICAL FIBER WITH SMOOTH TIP

RELATED APPLICATIONS

This application is related to U.S. Provisional Application No. 61/904,569, filed Nov. 15, 2013, to which priority is claimed and the entire disclosure of which is herein incorporated by reference.

FIELD OF THE INVENTION

The field of the present invention relates to endoscopes and to optical fibers contained within such endoscopes which are utilized in medical and other procedures for light-based, primarily laser-based, treatment of internal bodily organs.

BACKGROUND

It is a known technique to introduce an endoscopic instrument into the internal organs of a human for the purposes of either observation and/or the treatment of such internal organs. In a known manner, an endoscope is introduced into the body. Typically, the endoscope is a hollow tube of a specified dimension which is able to be introduced into a particular body organ. Endoscopes are well-known in the medical art and are used to perform various procedures, such as removal of tissue samples, observing the bodily organ, and performing laser-based procedures.

One procedure which is well-known is the introduction of an endoscope and an included laser fiber to break up, for example, kidney stones. Typically, as shown in FIG. 1, the distal end of the laser fiber is flat and orthogonal to the axis of the laser fiber. One reason for this is that the operator of the laser device wants to be able to manipulate the laser fiber within the endoscope so that it fires, when actuated, in the direction to which the fiber points. There are, however, a number of problems that exist in the art with the use of so-called flat face laser fibers.

One of these problems is that while the endoscope interior may be smooth, the flat tip possesses an edge all about the periphery of the flat tip which may get caught or stuck within the endoscope, particularly when the endoscope must be made to bend to be able to enter the internal passages of the human body and into, for example, the human kidney. Also, due to the fiber being of a very small diameter, for that very reason it presents sharp edges that may get caught in or perforate the endoscope. The flat tip has been known in the past to perforate the endoscope tube itself, which causes a number of problems in the procedure, including the entry of bodily fluids into the endoscope and damage to the flat tip edges which may affect the aiming of the laser beam. Even if the flat tip does not perforate the endoscope tube, the flat tip has been found to get partially stuck within the tube particularly around corners, and this causes problems in the operator's handling of the laser fiber as it is maneuvered within the endoscope and positioning within the body organ such as a kidney. It is known in the field of catheters and laser fibers that a skilled operator may maneuver in position the catheter or laser fiber largely at least partially by its "feel" and when the flat laser tip engages the inner walls of the endoscope that feel and feedback may be compromised.

Thus, the problem exists that while a flat tip is desirable if not necessary for a laser-based application requiring firing of the laser along the axis of the laser fiber, the very use of a flat tip laser fiber through an endoscope can cause any one a more the problems discussed above. Therefore, there is a need for a solution to this problem, so that a flat tip is presented when it exits the endoscope for treatment purposes yet does not get hung up within the endoscopic tube.

SUMMARY OF THE PRESENT INVENTION

In one aspect, a laser fiber may have a distal end and a laser fiber face; a tip addition is attached to the laser fiber face; the material of the tip addition may include a material which absorbs laser energy and one of fragments and melts; upon sending laser energy through the laser to the laser fiber face and to the tip addition, the tip addition one of fragments and melts.

In another aspect, the tip addition may be of a diameter of equal to or greater than the diameter of the laser fiber.

In another aspect, the tip addition material may be selected from one or more of: epoxy, acrylate and UV-cured glues.

In another aspect, the tip addition material may be curable with UV energy.

In yet another aspect, the tip addition on the laser fiber face may form a smooth surface. The tip addition may have a spherical surface.

In another aspect, the tip addition diameter may be selected to be greater than the diameter of the laser fiber but of lesser diameter than the interior of an endoscope tube into which it is inserted.

In another aspect, a method of treating human tissue with a laser includes: providing a laser fiber; attaching a tip addition to the distal end of the laser fiber; the tip addition may be one of frangible or meltable upon the application of laser energy through the laser fiber; inserting the laser fiber into an endoscope tube; extending the laser fiber out of the endoscope tube; applying laser energy through the laser fiber to impinge on the tip addition and cause the tip addition to one of fragment and melt; and providing laser treatment to the human tissue.

DETAILED DESCRIPTION OF THE INVENTION

Figure 1:
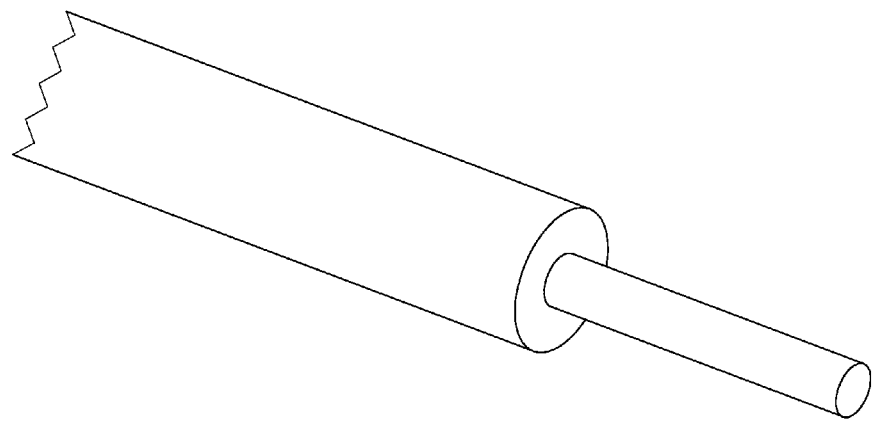
FIG. 1 is an illustration of a prior art flat tip laser fiber.

Referring now to the drawing FIG. 1, that figure as noted above shows a prior art embodiment in which the laser fiber possesses a flat tip. As can be seen from the drawing, the sharp edges surrounding the face of the flat tip can get caught on the inner tube of the endoscope causing difficulty in maneuvering the laser fiber or, as mentioned above, even perforate the endoscopic tube, causing a disruption if not an abandonment of the medical procedure being performed. In addition, depending on the strength of the laser fiber materials versus the endoscopic material, collision of the sharp edges of the flat fiber tip with the interior of the endoscope may cause the fiber tip face to chip or become scratched due to the collision with the endoscope interior, and this may cause the laser beam when activated to not fire in a direction along the axis of the laser beam which may cause unintended damage to the bodily organ under treatment.

Figure 2:
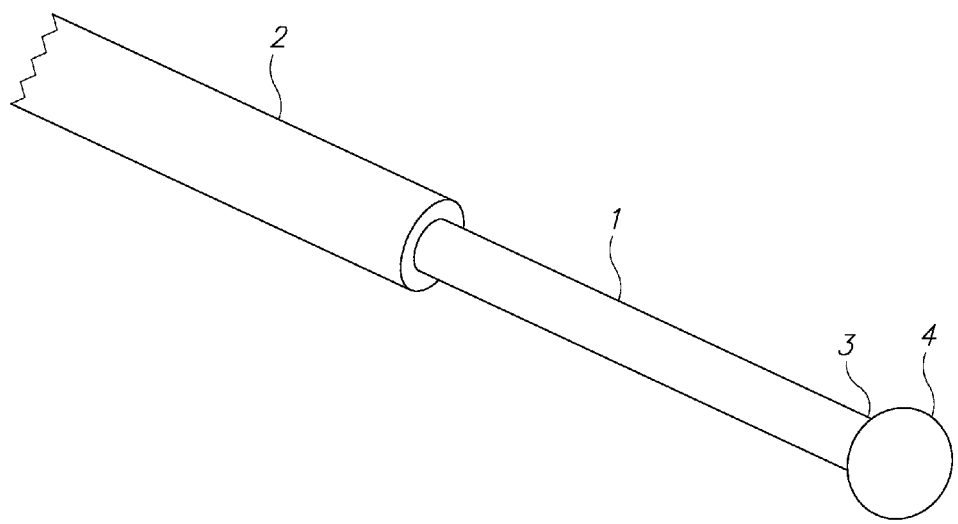
FIG. 2 is an illustration of an embodiment of the present invention.
Figure 3:
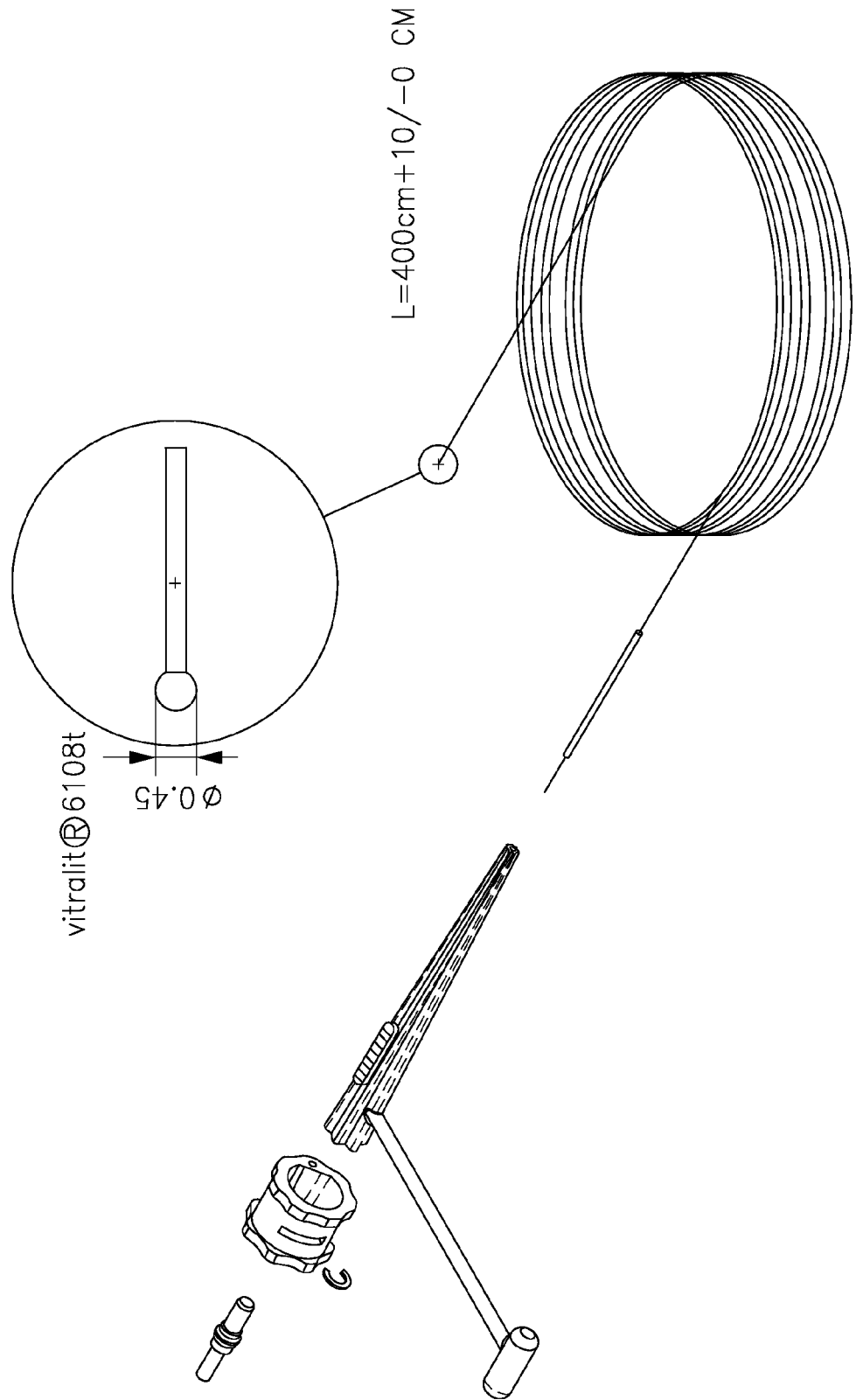
FIG. 3 is an illustration of the apparatus into which an embodiment of the present invention is associated.

Thus, what is needed is a device in which the face of the laser fiber while going through the endoscope is not flat with sharp edges yet when in operation possesses a flat face for the purposes of accurately directing the laser beam. It is clear that given the limited access within an endoscopic tube that a smooth cap which is somehow mechanically removable is not feasible. Turning now to FIG. 2, the figure illustrates one aspect of the present invention. As can be seen, a laser fiber 1 is contained with a shrinkwrap jacket 2. At the flat face end 3 of the laser fiber 1, a spherical tip 4 has been attached by suitable means to the end the laser fiber. Of course, while shown in the drawing as being spherical, the addition to the tip can be of any suitable shape, the desire and design being that the tip addition is smooth and does not have sharp edges which may interfere with the passage of the laser fiber through the endoscope. The tip addition may be, as shown on FIG. 2, of a diameter greater than that of the laser fiber, but may also be of a diameter the same as a lesson that of the laser fiber, so long as the tip addition engaging the interior of the endoscope is smooth rather than sharp. FIG. 3 illustrates the dimensions of the tip with respect to its fiber as well as the tip used in conjunction with a known optical fiber of the assignee of the present invention.

The tip addition may be attached to the flat face of the laser tip in any number of known ways. It may be, for example, glued to the flat face of the laser fiber, or even more simply the tip addition may itself be a dab of glue which is formed into a spherical or other smooth shape. The dab of glue may be applied to the flat face end of the laser fiber in a non-cured form which, when cured, would present a smooth surface due to surface tension as well as become attached to the flat face of the laser fiber. The question then remains as to how the tip addition is removed when the endoscope is in place and the laser fiber extended ready for the application of a laser beam through the fiber to the target tissue. The tip addition may be made of a material that will be either shattered or melted or otherwise destroyed when a suitable laser beam is applied to the laser fiber. Once the tip addition removed by either being shattered or otherwise destroyed, the flat face of the laser beam may then be applied to the target tissue. One glue which has been found to perform well is Vitralit® 6108T, available from Panocol of Taunus, Germany, but this is by way of example only and other glues or other materials may be used as well. The material chosen for the tip addition preferably is one which would have a high absorption capacity for the laser beam that impinges on it from the fiber tip end face. Otherwise, the beam would pass through the tip addition without destroying the tip addition which may cause less effective treatment of the target tissue due to light scattering and partial absorption of the laser beam energy by the tip addition.

The tip addition may, as disclosed above, comprise a glue-like substance, but also may be of any material which, upon the application of a laser beam to the material, would fracture or otherwise melt or disintegrate. One suitable glue which may be selected is one of the Vitralit® family of glues, including Vitralit® 6108T. Other suitable materials may include materials which absorb IR wavelengths such as: epoxy, acrylate, and UV-cured glues, or any type of polymeric material in a liquid amorphic phase that may then be cured. The materials selected for the tip addition may vary in composition depending upon the particular wavelength and power of the laser beam applied to the flat end of the laser fiber. A suitable tip addition material for use with a laser of 2100 nm may selected from epoxy materials, acrylate materials and UV-cured glues. However, any suitable material may be chosen so long as that material is shattered, melted or otherwise destroyed by the laser beam. The material may be transparent to allow for some visualization by the operator, or the tip addition material may be comprised of a non-transparent material that would better absorb the laser beam energy and fracture or otherwise be destroyed.

Curing of the tip addition onto the fiber end face may be performed in any number of ways. For example, one or a plurality of fibers may be placed in a suitable holding apparatus, an amount of glue placed at the fiber end face and then suitable energy, for example, laser energy, used to cure the tip addition. In addition, a suitable energy source, including a laser source, may be applied to the distal end of the fiber, travel through the fiber to the fiber face and impinge on and cure a drop of glue which has been placed on the fiber end face.

By way of example only, if the fiber is of a diameter of 230µ, the tip addition may be of a diameter of 450µ, although the tip addition will, of course, need to be small enough to fit within the interior of the endoscope tube.

EXAMPLE 1

An endoscope of interior diameter 3.6FR was chosen. A laser fiber of outside diameter 400 um was also selected. The distal end of the laser fiber was finished with a flat face and a dab of glue comprising Vitralit® and of diameter 450 um affixed to the flat face and the dab of glue cured. The laser fiber was then introduced into the endoscope tube. It was then observed that the laser fiber moved through the endoscope without causing damage to the endoscope or getting hung up within the endoscope. The end of the laser fiber was passed all the way through the endoscope tube until it exited the end of the tube and could be observed. A laser beam of 2100 nm and a minimum power of 0.26 J was then passed through the laser fiber and was observed to shatter the tip addition.

The above example is but one example of the ways in which the tip addition may be utilized. Other diameter laser fibers, other diameter tip additions, other material tip additions and other lasers may be used within the scope of the present invention. While the tip addition is shown in FIG. 2 as spherical, the tip addition may be hemispherical and of the same or greater than or less than the diameter of the laser fiber.

We claim:

1. A laser fiber, wherein the laser fiber has a distal end having a laser fiber face;
   a tip addition attached to the laser fiber face;
   the material of the tip addition comprising a material which absorbs laser energy and one or more of fragments and melts;
   wherein, upon impingement of laser energy through the laser to the laser fiber face and to the tip addition, the tip addition one or more of fragments and melts; and, wherein the tip addition is formed in one of a: spherically-shaped surface, a hemispherically-shaped surface or a curved-shaped surface.

2. The laser fiber of claim 1 wherein the tip addition is of a diameter of equal to or greater than the diameter of the laser fiber.

3. The laser fiber of claim 1 wherein the tip addition material is selected from one or more of: epoxy, acrylate and UV-cured glues.

4. The laser fiber of claim 3 wherein the tip addition material is curable with UV energy.

5. The laser fiber of claim 1, wherein the tip addition on the laser fiber face is formed with a smooth surface.

6. The laser fiber of claim 5, wherein the tip addition is selected from one or more of: an epoxy, an acrylate, or an UV-cured glue.

7. The laser fiber of claim 1, wherein the tip addition is selected to be greater than the diameter of the laser fiber but of lesser diameter than the interior of an endoscople tube into which it is inserted.

8. The laser fiber of claim 1, wherein the tip addition is formed of a material which absorbs IR wavelengths of light.

9. The laser fiber of claim 1, wherein the tip addition is formed of a material which absorbs laser energy.

10. The laser fiber of claim 1, wherein the tip addition comprises a material which is one or transparent, translucent or non-transparent.

11. A method of treating human tissue with a laser, comprising:
    providing a laser fiber;
    attaching a tip addition to the distal end of the laser fiber, the tip addition being one of a frangible or meltable upon the application of laser energy through the laser fiber;
    inserting the laser fiber into an endoscope tube;
    extending the laser fiber out of the endoscope tube;
    applying laser energy through the laser fiber to impinge on the tip addition and cause the tip addition to one of fragment and melt; and
    providing laser treatment to the human tissue; and,
    wherein the tip addition is formed in one of a: spherically-shaped surface, a hemispherically-shaped surface or a curved-shaped surface.

12. The method of claim 11, wherein the step of attaching a tip addition comprises placing material for the tip addition on the laser fiber face and providing laser energy through the laser fiber to cure the material of the tip addition onto the laser fiber face.

13. The method of claim 11, wherein the tip addition is selected from one or more of: an epoxy, an acrylate, or an UV-cured glue.

14. A method of protecting a fiber being inserted into an endoscope tube and extended out of the endoscope tube comprising the steps of:
    providing a laser fiber having a substantially flate face tip with a smooth tip addition, the tip addition being of a material one of frangible or meltable upon the application of laser energy through the laser fiber;
    inserting the laser fiber into an endoscope;
    extending at least the tip of the laser fiber out of the endoscope tube;
    applying laser energy through the laser fiber to impinge on the tip addition and to cause the tip addition to one of fragment and melt, thereby removing the tip addition and providing the flat face tip ready for the application of a laser beam through the fiber to a target tissue; and,
    wherein the tip addition is formed in one of a spherically-shaped surface, a hemispherically-shaped surface or a curved-shaped surface.

15. The method of claim 14 wherein the tip addition is of a diameter of equal to or greater than the diameter of the laser fiber.

16. The method of claim 14 wherein the tip addition material is selected from one or more of: epoxy, acrylate and UV-cured glues.

* * * * *

UNITED STATES PATENT AND TRADEMARK OFFICE
CERTIFICATE OF CORRECTION

PATENT NO.        : 9,968,404 B2
APPLICATION NO.   : 14/541038
DATED             : May 15, 2018
INVENTOR(S)       : Naim Ashraf, George Kuka and Arkady Khachaturov Page 1 of 1

It is certified that error appears in the above-identified patent and that said Letters Patent is hereby corrected as shown below:

In the Claims

In Claim 3, Line 1, add "," after --1--.

In Claim 4, Line 1, add "," after --1--.

In Claim 7, Line 1, "endoscople" should be --endoscope--.

In Claim 10, Line 2, "or" should be --of:--.

In Claim 11, Line 4, delete "a".

In Claim 14, Line 4, "flate" should be --flat--.

In Claim 14, Line 12, "of" should be --of:--.

Signed and Sealed this
Ninth Day of October, 2018

Andrei Iancu
*Director of the United States Patent and Trademark Office*